(12) United States Patent
Chien (10) Patent No.: US 10,380,420 B2
(45) Date of Patent: Aug. 13, 2019

(54) ELECTRONIC DEVICE AND SCREEN ADJUSTING METHOD BASED ON CONDITION OF USER'S EYE

(71) Applicant: HON HAI PRECISION INDUSTRY CO., LTD., New Taipei (TW)

(72) Inventor: Cheng-Ching Chien, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 264 days.

(21) Appl. No.: 15/468,054

(22) Filed: Mar. 23, 2017

(65) Prior Publication Data

US 2017/0286745 A1    Oct. 5, 2017

(30) Foreign Application Priority Data

Apr. 5, 2016  (TW) .............................. 105110676 A (51) Int. Cl.
| | |
|---|---|
| G09G 5/10 | (2006.01) |
| G09G 5/02 | (2006.01) |
| A61B 3/117 | (2006.01) |
| G06F 3/048 | (2013.01) |
| G06F 3/147 | (2006.01) |
| G06F 3/00 | (2006.01) |
| G06F 3/01 | (2006.01) |

(Continued)

(52) U.S. Cl.
CPC .......... *G06K 9/0061* (2013.01); *A61B 3/1176* (2013.01); *G06F 3/005* (2013.01); *G06F 3/013* (2013.01); *G06F 3/048* (2013.01); *G06F 3/147* (2013.01); *G06K 9/00604* (2013.01); *G06T 7/0012* (2013.01); *G06T 7/90* (2017.01); *G09G 5/02* (2013.01); *G09G 5/10* (2013.01); *G06T 2207/10024* (2013.01); *G06T 2207/30041* (2013.01); *G09G 3/3406* (2013.01); *G09G 2320/0626* (2013.01); *G09G 2320/0666* (2013.01); *G09G 2330/027* (2013.01); *G09G 2354/00* (2013.01)

(58) Field of Classification Search
CPC .......... A61B 3/11; A61B 3/112; A61B 3/107; A61B 3/1035; A61B 3/036; A61B 3/085; A61B 3/1176

See application file for complete search history.

(56) References Cited

U.S. PATENT DOCUMENTS

| | | | | |
|---|---|---|---|---|
| 5,990,973 | A * | 11/1999 | Sakamoto | ............ G06K 9/0061 348/246 |
| 7,827,426 | B2 * | 11/2010 | Burnett | .................... H04N 5/63 713/300 |

(Continued)

OTHER PUBLICATIONS

Patwari MA, Arif MD, Chowdhury MN, Arefin A, Imam MI. Detection, categorization, and assessment of eye cataracts using digital image processing. InThe first international conference on interdisciplinary research and development May 2011 (pp. 22-1). (Year: 2011).*

*Primary Examiner* — Clifford Hilaire
(74) *Attorney, Agent, or Firm* — ScienBiziP, P.C.

(57) ABSTRACT

A method for adjusting a display screen of an electronic device is disclosed. The method includes obtaining a pupil image of a user of the electronic device. An eye condition of the user is determined by analyzing the pupil image. The proportions between a red channel, a green channel, and a blue channel (RGB) of a display screen of the electronic device is adjusted according to the eye condition.

12 Claims, 5 Drawing Sheets

(51) Int. Cl.
*G09G 3/34* (2006.01)
*G06K 9/00* (2006.01)
*G06T 7/00* (2017.01)
*G06T 7/90* (2017.01)

(56) References Cited

U.S. PATENT DOCUMENTS

| | | | |
|---|---|---|---|
| 9,298,020 B1* | 3/2016 | Etzkorn | G02C 7/04 |
| 2012/0188508 A1* | 7/2012 | Kim | A61B 3/103 |
| | | | 351/206 |
| 2015/0268721 A1* | 9/2015 | Joo | G02B 27/0093 |
| | | | 345/156 |
| 2016/0080720 A1* | 3/2016 | Fullam | H04N 13/398 |
| | | | 345/156 |
| 2016/0270656 A1* | 9/2016 | Samec | A61B 3/085 |

* cited by examiner

ELECTRONIC DEVICE AND SCREEN ADJUSTING METHOD BASED ON CONDITION OF USER'S EYE

CROSS-REFERENCE TO RELATED APPLICATIONS

This application claims priority to Taiwanese Patent Application No. 105110676 filed on Apr. 5, 2016, the contents of which are incorporated by reference herein.

FIELD

The subject matter herein generally relates to managing technology, and particularly to an electronic device and a method for adjusting a display screen of the electronic device.

BACKGROUND

Improper or extended use of an electronic device may cause deterioration of a user's eyesight.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The present disclosure, referencing the accompanying drawings, is illustrated by way of examples and not by way of limitation. It should be noted that references to "an" or "one" embodiment in this disclosure are not necessarily to the same embodiment, and such references mean "at least one."

Furthermore, the term "module", as used herein, refers to logic embodied in hardware or firmware, or to a collection of software instructions, written in a programming language, such as Java, C, or assembly. One or more software instructions in the modules can be embedded in firmware, such as in an EPROM. The modules described herein can be implemented as either software and/or hardware modules and can be stored in any type of non-transitory computer-readable medium or other storage device. Some non-limiting examples of non-transitory computer-readable media include CDs, DVDs, BLU-RAY, flash memory, and hard disk drives.

Figure 1:
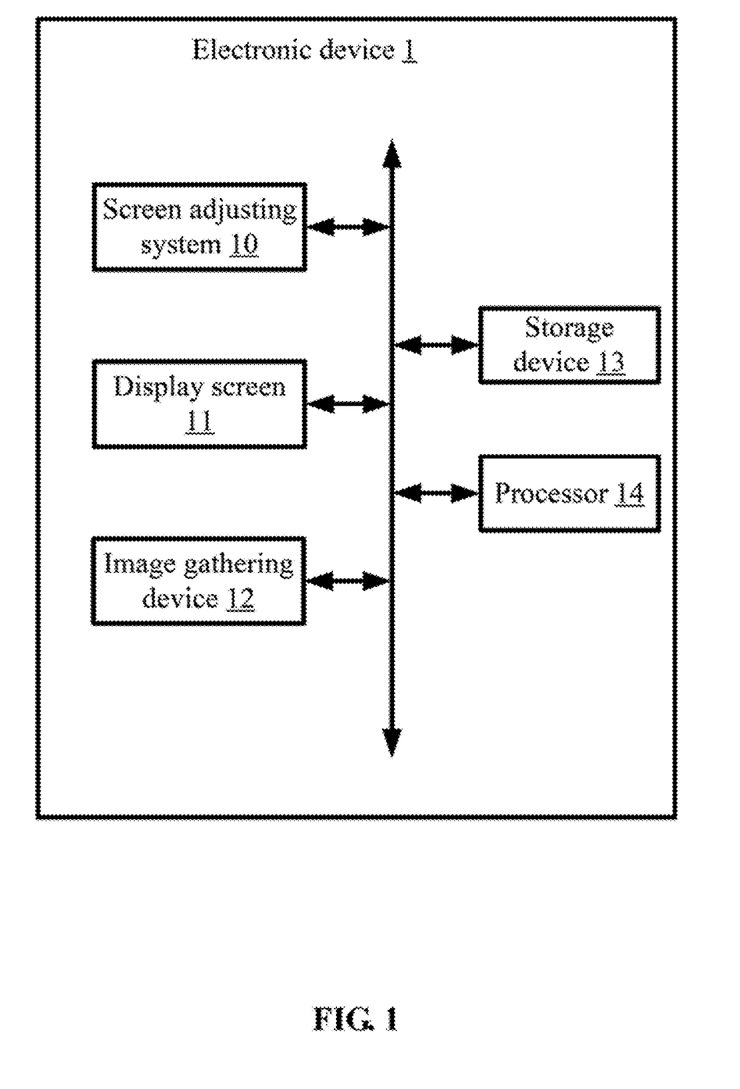
FIG. 1 is a block diagram of one exemplary embodiment of an electronic device including a screen adjusting system.

FIG. 1 is a block diagram of one embodiment of an electronic device. Depending on the embodiment, an electronic device 1 can include, but is not limited to, a screen adjusting system 10, a display screen 11, an image gathering device 12, a storage device 13, at least one processor 14. In at least one exemplary embodiment, the electronic device 1 can be a mobile phone, a tablet computer, a personal digital assistant, or any other suitable device such as a smart television. FIG. 1 illustrates only one example of the electronic device 1, other examples can include more or fewer components than illustrated, or have a different configuration of the various components in other exemplary embodiments.

In at least one exemplary embodiment, the screen adjusting system 10 adjusts the display screen 11 according to an eye condition of a user of the electronic device 1. For example, when the user of the electronic device 1 is determined to be old, because of age-related cataracts for example, the screen adjusting system 10 can adjust proportions between a red channel, a green channel, and a blue channel (hereinafter "proportions between RGB") of the display screen 11 by decreasing the blue channel.

In at least one exemplary embodiment, the image gathering device 12 can be a camera device or a human face scanner. The image gathering device 12 can be used to capture images of the user of the electronic device 1. In at least one exemplary embodiment, the image gathering device 12 can be integrated in the electronic device 1. For example, the image gathering device 12 can be a built-in front-facing camera of the electronic device 1. In other exemplary embodiments, the image gathering device 12 can be externally connected with the electronic device 1. For example, the image gathering device 12 can connect with the electronic device 1 using a universal serial bus (USB).

In at least one exemplary embodiment, the storage device 13 can be a memory of the electronic device 1. In other exemplary embodiments, the storage device 13 can be a secure digital card, or other external storage device such as a smart media card. The storage device 13 can be used to store data of the electronic device 1.

The at least one processor 14 can be a central processing unit (CPU), a microprocessor, or other data processor chip that performs functions of the electronic device 1.

Figure 2:
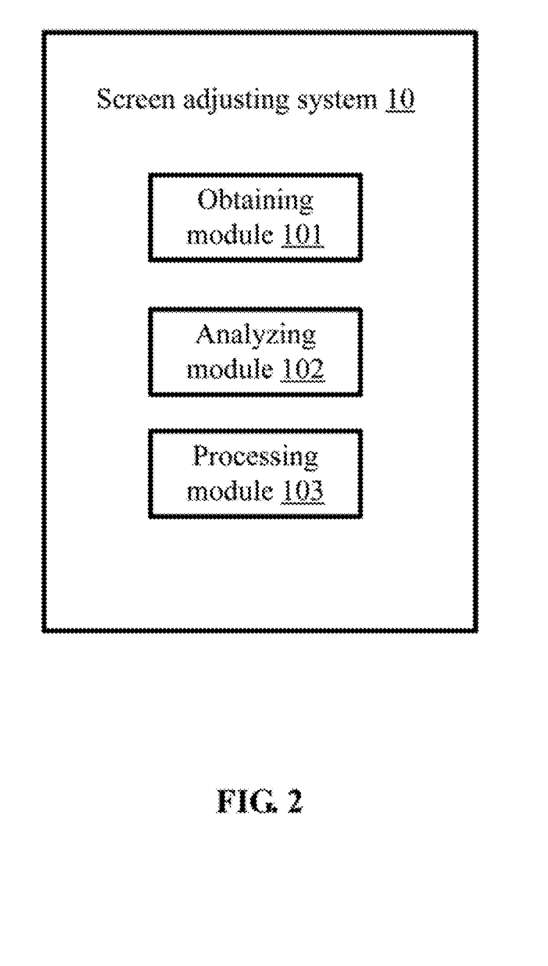
FIG. 2 is a block diagram of one exemplary embodiment of modules of the screen adjusting system of FIG. 1.

FIG. 2 illustrates a block diagram of one exemplary embodiment of modules of the screen adjusting system 10. In at least one exemplary embodiment, the screen adjusting system 10 can include an obtaining module 101, an analyzing module 102, and a processing module 103. The modules 101-103 include computerized codes in the form of one or more programs that may be stored in the storage device 13. The computerized codes include instructions that can be executed by the at least one processor 14.

The obtaining module 101 can obtain an image of pupil (hereinafter "pupil image") of the user of the electronic device 1.

In at least one exemplary embodiment, the obtaining module 101 can control the image gathering device 12 to capture an image of the user. The obtaining module 101 can recognize a face area from the image of the user using a preset face recognition method. The obtaining module 101 can recognize an eye area from the face area using a preset eye recognition method. The obtaining module 101 can recognize a pupil area from the eye area, and clip or extract the pupil area from the eye area to obtain the pupil image.

In at least one exemplary embodiment, the preset face recognition method can include, but is not limited to, a face template matching method, or a skin template matching method. The preset eye recognition method can include, but is not limited to, a Hough Transform method, or a template-deformation method. In at least one exemplary embodiment, the obtaining module 101 can recognize the pupil area from the eye area by comparing the eye area with a preset pupil image template. When an area of the eye area matches with the preset pupil image template, the obtaining module 101 can determine the area is the pupil area.

The analyzing module 102 can determine an eye condition of the user by processing and analyzing the pupil image.

In at least one exemplary embodiment, the analyzing module 102 can process the pupil image using a high-contrast and low-light image processing method and obtain a processed pupil image. The analyzing module 102 can analyze the processed pupil image by analyzing a grayscale and chrominance variances of the processed pupil image.

Figure 3A:
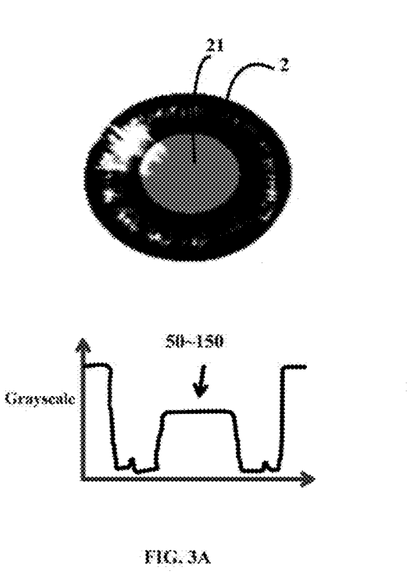
FIGS. 3A-3D illustrate examples of identifying an eye condition of a user.

In at least one exemplary embodiment, as illustrated in FIG. 3A, when the analyzing module 102 determines that the grayscale of a middle portion 21 of a pupil image 2 is within a first preset range such as [50 to 150], the analyzing module 102 can determine that the eye of the user has cataract, i.e., the user has an eye disease. The analyzing module 102 can determine that the eye of the user is not normal.

Figure 3B:
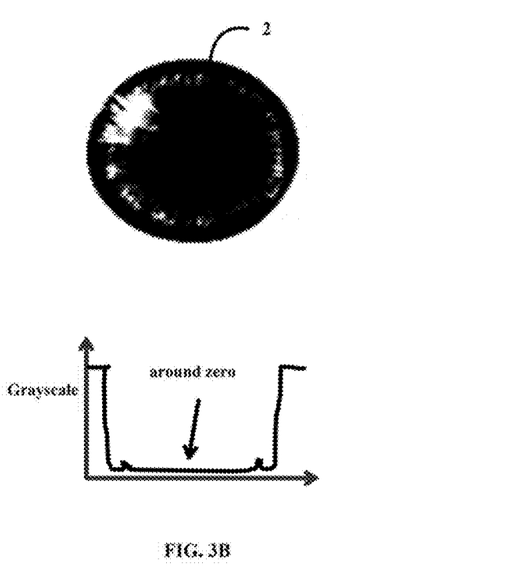

In at least one exemplary embodiment, as illustrated in FIG. 3B, when the analyzing module 102 determines that the grayscale of the middle portion 21 is within a second preset range around zero, the analyzing module 102 can determine that the eye of the user is in a normal state, i.e., the user does not have an eye disease.

Figure 3C:
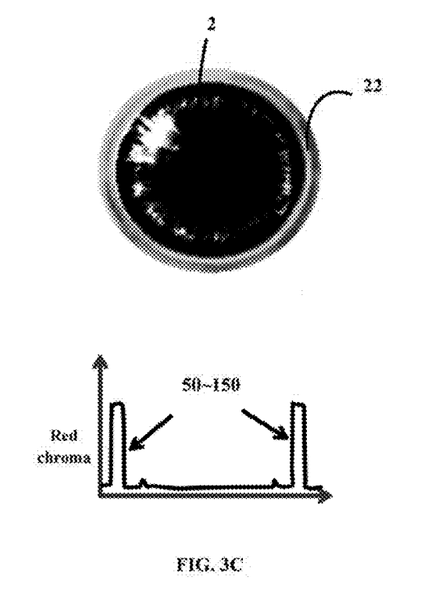

In at least one exemplary embodiment, as illustrated in FIG. 3C, when the analyzing module 102 determines that a red chroma of a side portion 22 is within a third preset range such as [50 to 150], the analyzing module 102 can determine that the eye of the user is pinkeye, i.e., the user has an eye disease. The analyzing module 102 can determine that the eye of the user is not normal.

Figure 3D:
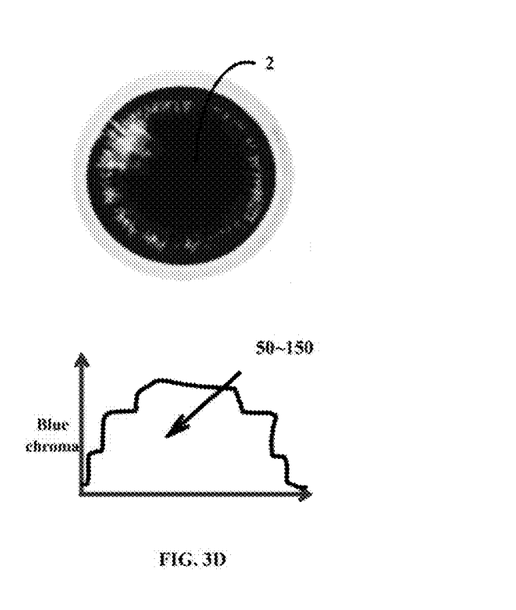

In at least one exemplary embodiment, as illustrated in FIG. 3D, when the analyzing module 102 determines that a blue chroma of the pupil image 2 is within a fourth preset range such as [50 to 150], the analyzing module 102 can determine that the user is wearing contact lens(es). The analyzing module 102 can determine that the eye of the user is not normal.

The processing module 103 can adjust the display screen 11 according to the determined eye condition.

In at least one exemplary embodiment, when the eye of the user is in the normal state, the processing module 103 makes no change to the display screen 11, i.e., the processing module 103 does not adjust the display screen 11.

In at least one exemplary embodiment, the processing module 103 can adjust the display screen 11 by adjusting the proportions between RGB when the eye of the user is deemed not normal.

For example, when the analyzing module 102 determines that the user has an eye disease, the processing module 103 can decrease the blue channel of the display screen 11 to allow the user to look at the display screen 11 more comfortably.

In at least one exemplary embodiment, when the analyzing module 102 determines that the user is wearing contact lens(es), the processing module 103 can record a start time when the user begins to watch the display screen 11 while wearing the contact lens(es). The processing module 103 can calculate a time length of the user wears the contact lens(es) based on the start time. When the time length is equal to or greater than a preset time length (for example, 4 hours), the processing module 103 can transmit a prompt. For example, the processing module 103 can display a preset message such as "please remove your contact lens(es)", and/or play a preset warning audio message.

In at least one exemplary embodiment, when the analyzing module 102 determines that the user is wearing contact lens(es), the processing module 103 can obtain a current time of the electronic device 1, and set the current time as the start time.

In other exemplary embodiments, the processing module 103 can provide a user interface and record the start time in response to a user input.

In at least one exemplary embodiment, the obtaining module 101 obtains pupil images of the user from the start time. When the user is determined to be wearing contact lens(es) in each pupil image obtained during the preset time length, the processing module 103 can determine that the user is wearing contact lens(es) for the preset time length. The processing module 103 can transmit the prompt.

In other exemplary embodiments, the obtaining module 101 can obtain a pupil image of the user when a time length from the start time equals the preset time length. When the analyzing module 102 determines that the user is wearing contact lens(es) in the pupil image, the analyzing module 102 determines that the user is wearing contact lens(es) for the preset time length, and the processing module 103 can transmit the prompt. That is, in the other exemplary embodiments, only one pupil image is used for determining whether the user is wearing contact lens(es) for the preset time length.

In other exemplary embodiments, the obtaining module 101 can obtain a first pupil image of the user when the start time is recorded. The obtaining module 101 can obtain a second pupil image of the user when a time length calculated from the start time equals the preset time length. When the analyzing module 102 determines that the user is wearing contact lens(es) in the first pupil image and the second pupil image, the analyzing module 102 determines that the user has been wearing contact lens(es) for the preset time length, and the processing module 103 can transmit the prompt. That is, only two pupil images are used for determining whether the user is wearing contact lens(es) for the preset time length.

In at least one exemplary embodiments, the processing module 103 can adjust the display screen 11 according to changes in a diameter of the pupil (hereinafter "pupil diameter") of the user in the pupil image.

In at least one exemplary embodiments, the analyzing module 102 can determine the pupil diameter of the user in the pupil image using an image recognition algorithm. The processing module 103 can adjust a brightness value of a backlight of the display screen 11. For example, the processing module 103 can adjust the brightness value of the backlight of the display screen 11 when the pupil diameter of the user is determined to be in different preset ranges.

The pupil diameter of the user generally changes according to a brightness value of a surrounding environment. The pupil diameter of the user decreases when the brightness increases. Conversely, the pupil diameter of the user increases when the brightness decreases. In other words, the value of the pupil diameter of the user can represent the current brightness value of the surrounding environment. That is, the processing module 103 can adjust the brightness value of the backlight of the display screen 11 according to the pupil diameter of the user.

For a first example, when the analyzing module 102 determines that the value of pupil diameter of the user is greater than or equal to 2 mm and less than or equal to 3 mm (i.e., [2 to 3 mm]), the processing module 103 can determine that the user is in an environment with strong or bright light. The processing module 103 can increase a current brightness value of the backlight of the display screen 11. For a second example, when the analyzing module 102 determines that the value of pupil diameter of the user is greater than 3 mm and less than or equal to 5 mm (i.e., (3 to 5 mm]), the processing module 103 can determine that the user is in a comfortable environment. The processing module 103 can keep the current brightness value of the backlight of the display screen 11 or slightly adjust the current brightness value of the display screen 11. For a third example, when the analyzing module 102 determines that the value of pupil diameter of the user is greater than 5 mm and less than or equal to 8 mm (i.e., (5 to 8 mm]), the processing module 103 can determine that the user is in an environment with low light. The processing module 103 can decrease the current brightness value of the backlight of the display screen 11 to make it dimmer.

In at least one exemplary embodiment, to enable comfortable viewing, the processing module 103 can further adjust the display screen 11 according to eye actions. In at least one exemplary embodiment, the eye actions can include, but are not limited to, frowning, narrowing of the eyes, and closing the eyes.

In at least one exemplary embodiment, the obtaining module 101 can obtain eye images of the user in real-time.

It should be noted that the method of obtaining the eye image of the user is similar to the method of obtaining the pupil image. When the eye area is recognized from the face area, the obtaining module 101 can clip or extract the eye area from the face area, thus the eye image is obtained.

In at least one exemplary embodiment, the analyzing module 102 can determine the eye action by analyzing the eye image.

In at least one exemplary embodiment, the analyzing module 102 can pre-store a number of image templates. The number of image templates includes frown images, eye narrowing images, and eye closing images. The frown image can be defined as an image of eye area in which the user frowns. The eye narrowing image can be defined as an image of eye area in which the user narrows his eyes. The eye closing image can be defined as an image of eye area in which the user closes at least one eye. In at least one exemplary embodiment, the analyzing module 102 can determine that the user frowns in the eye image when the eye image matches one of the frown image templates. Similarly, the analyzing module 102 can determine that the user narrows eyes in the eye image when the eye image matches one of the eye narrowing image templates. The analyzing module 102 can determine that the user closes eyes in the eye image when the eye image matches one of the eye closing image templates.

In at least one exemplary embodiment, the processing module 103 can adjust the display screen 11 by adjusting the brightness value of the backlight of the display screen 11 and/or the proportions between RGB of the display screen 11 according to the determined eye action. For example, when the user is determined to be closing his/her eyes, the processing module 103 can inactivate the display screen 11 to save power.

In other exemplary embodiments, the analyzing module 102 can analyze whether the user has eye fatigue, and the processing module 103 can control the electronic device 1 accordingly to reduce eye fatigue.

In at least one exemplary embodiment, the analyzing module 102 can calculate a ratio between a first total number of red pixels of the eye image and a second total number of all pixels of the eye image. The analyzing module 102 can determine that the user has eye fatigue when such ratio is greater than a preset ratio (for example, 70%). The analyzing module 102 can determine that the user does not have eye fatigue when the ratio is less than or equal to the preset ratio.

In at least one exemplary embodiment, the analyzing module 102 can first find the red pixels from the eye image according to the RGB value of each of pixels of the eye image. The analyzing module 102 can calculate the first total number of the red pixels and the second total number of all pixels of the eye image. The analyzing module 102 can divide the first total number by the second total number to obtain the ratio.

In at least one exemplary embodiment, when the user is determined to be suffering from eye fatigue, the processing module 103 can further transmit a prompt. For example, the processing module 103 can display a preset message on the display screen 11 or can play a predetermined audio message such as "your eyes are fatigued, please have a rest".

It should be noted that when the user is lack of sleep, the eye area is bloodshot. Thus, the ratio can be used to determine whether the user has eye fatigue.

In at least one exemplary embodiment, when the user has eye fatigue, the processing module 103 can transmit the prompt to prompt the user to stop using the electronic device 1. The processing module 103 can control the electronic device 1 to enter a sleep state when the user has eye fatigue. In other exemplary embodiments, the processing module 103 can further wake up the electronic device 1 from the sleep state when the electronic device 1 is kept in the sleep state for a predetermined time length (for example, 10 minutes).

Figure 4:
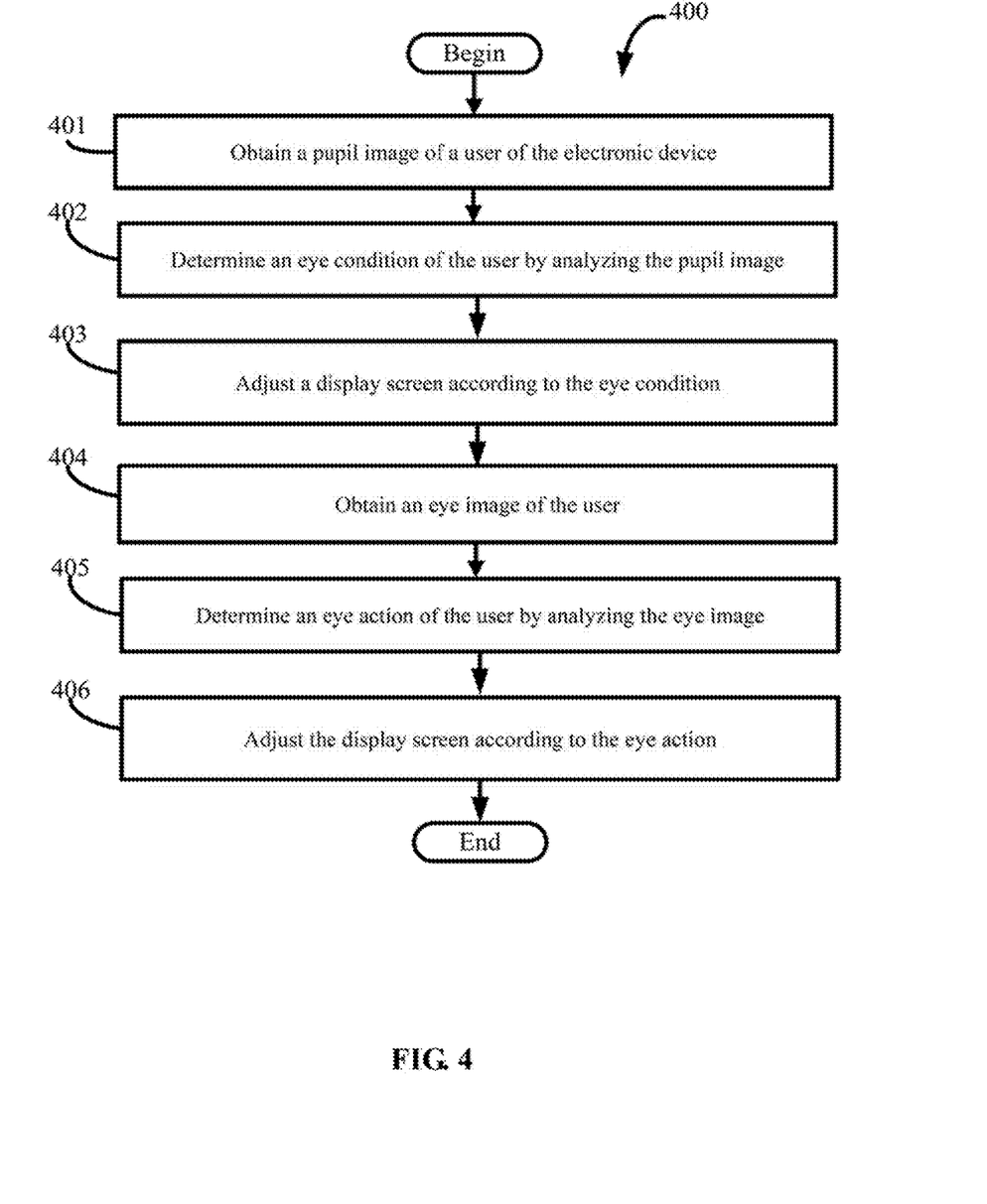
FIG. 4 illustrates a flow chart of one exemplary embodiment of a first method of adjusting a display screen of the electronic device of FIG. 1.

FIG. 4 illustrates a flowchart which is presented in accordance with an example embodiment. The exemplary method 400 is provided by way of example, as there are a variety of ways to carry out the method. The method 400 described below can be carried out using the configurations illustrated in FIG. 1, for example, and various elements of these figures are referenced in explaining exemplary method 400. Each block shown in FIG. 4 represents one or more processes, methods, or subroutines, carried out in the exemplary method 400. Additionally, the illustrated order of blocks is by example only and the order of the blocks can be changed according to the present disclosure. The exemplary method 400 can begin at block 401. Depending on the embodiment, additional steps can be added, others removed, and the ordering of the steps can be changed.

At block 401, the obtaining module 101 can obtain a pupil image of the user of the electronic device 1.

In at least one exemplary embodiment, the obtaining module 101 can control the image gathering device 12 to capture an image of the user. The obtaining module 101 can recognize a face area from the image of the user using a preset face recognition method. The obtaining module 101 can recognize an eye area from the face area using a preset eye recognition method. The obtaining module 101 can recognize a pupil area from the eye area, and clip or extract the pupil area from the eye area to obtain the pupil image.

In at least one exemplary embodiment, the preset face recognition method can include, but is not limited to, a face template matching method, or a skin template matching method. The preset eye recognition method can include, but is not limited to, a Hough Transform method, or a template-deformation method. In at least one exemplary embodiment, the obtaining module 101 can recognize the pupil area from the eye area by comparing the eye area with a preset pupil image template. When an area of the eye area matches with the preset pupil image template, the obtaining module 101 can determine the area is the pupil area.

At block 402, the analyzing module 102 can determine an eye condition of the user by processing the pupil image and analyzing the processed pupil image.

In at least one exemplary embodiment, the analyzing module 102 can process the pupil image using a high-contrast and low-light image processing method and obtain a processed pupil image. The analyzing module 102 can analyze the processed pupil image by analyzing a grayscale and chrominance variances of the processed pupil image.

In at least one exemplary embodiment, as illustrated in FIG. 3A, when the analyzing module 102 determines that the grayscale of a middle portion 21 of a pupil image 2 is within a first preset range such as [50 to 150], the analyzing module 102 can determine that the eye of the user has cataract, i.e., the user has an eye disease. The analyzing module 102 can determine that the eye of the user is not normal.

In at least one exemplary embodiment, as illustrated in FIG. 3B, when the analyzing module 102 determines that the grayscale of the middle portion 21 is within a second preset range around zero, the analyzing module 102 can determine that the eye of the user is in a normal state, i.e., the user does not have an eye disease.

In at least one exemplary embodiment, as illustrated in FIG. 3C, when the analyzing module 102 determines that a red chroma of a side portion 22 is within a third preset range such as [50 to 150], the analyzing module 102 can determine that the eye of the user is pinkeye, i.e., the user has eye disease. The analyzing module 102 can determine that the eye of the user is not normal.

In at least one exemplary embodiment, as illustrated in FIG. 3D, when the analyzing module 102 determines that a blue chroma of the pupil image 2 is within a fourth preset range such as [50 to 150], the analyzing module 102 can determine that the user is wearing contact lens(es)es. The analyzing module 102 can determine that the eye of the user is not normal.

At block 403, the processing module 103 can adjust the display screen 11 according to the determined eye condition.

In at least one exemplary embodiment, when the eye of the user is in the normal state, the processing module 103 can make no change to the display screen 11, i.e., the processing module 103 does not adjust the display screen 11.

In at least one exemplary embodiment, the processing module 103 can adjust the display screen 11 by adjusting the proportions between RGB when the eye of the user is deemed not normal.

For example, when the analyzing module 102 determines that the user has an eye disease such as cataract or pinkeye, the processing module 103 can decrease the blue channel of the display screen 11 to enable the user to look at the display screen 11 more comfortably.

In at least one exemplary embodiment, when the analyzing module 102 determines that the user is wearing contact lens(es), the processing module 103 can record a start time when the user begins to watch the display screen 11 while wearing the contact lens(es). The processing module 103 can calculate a time length of the user wears the contact lens(es) based on the start time. When the time length is equal to or greater than a preset time length (for example, 4 hours), the processing module 103 can transmit a prompt. For example, the processing module 103 can display a preset message such as "please remove your contact lens(es)", or play a preset warning audio message.

In at least one exemplary embodiment, when the analyzing module 102 determines that the user is wearing contact lens(es), the processing module 103 can obtain a current time of the electronic device 1, and set the current time as the start time. In other exemplary embodiments, the processing module 103 can provide a user interface and record the start time in response to a user input.

In at least one exemplary embodiment, the obtaining module 101 obtains pupil images of the user from the start time. When the user is determined to be wearing contact lens(es) in each pupil image obtained during the preset time length, the processing module 103 can determine that the user is wearing contact lens(es) for the preset time length. The processing module 103 can transmit the prompt.

In other exemplary embodiments, the obtaining module 101 can obtain a pupil image of the user when a time length calculated from the start time equals the preset time length. When the analyzing module 102 determines that the user is wearing contact lens(es) in the pupil image, the analyzing module 102 determines that the user wears contact lens(es) for the preset time length, and the processing module 103 can transmit the prompt. That is, in the other exemplary embodiments, only one pupil image is used for determining whether the user wears contact lens(es) for the preset time length.

In other exemplary embodiments, the obtaining module 101 can obtain a first pupil image of the user when the start time is recorded. The obtaining module 101 can obtain a second pupil image of the user when a time length calculated from the start time equals the preset time length. When the analyzing module 102 determines that the user is wearing contact lens(es) in the first pupil image and the second pupil image, the analyzing module 102 determines that the user has been wearing contact lens(es) for the preset time length, and the processing module 103 can transmit the prompt. That is, only two pupil images are used for determining whether the user is wearing contact lens(es) for the preset time length.

In at least one exemplary embodiments, the processing module 103 can adjust the display screen 11 according to a pupil diameter of the user in the pupil image.

In at least one exemplary embodiments, the analyzing module 102 can determine the pupil diameter of the user in the pupil image using an image recognition algorithm. The processing module 103 can adjust a brightness value of the backlight of the display screen 11. For example, the processing module 103 can adjust the brightness value of the backlight of the display screen 11 when the pupil diameter of the user is determined to be in different preset ranges.

The pupil diameter of the user generally changes according to a brightness value of a surrounding environment. The pupil diameter of the user decreases when the brightness value of the surrounding environment increases. Conversely, the pupil diameter of the user increases when the brightness value of the surrounding environment decreases. In other words, the value of the pupil diameter of the user can represent the current brightness value of the surrounding environment. That is, the processing module 103 can adjust the brightness value of the backlight of the display screen 11 according to the pupil diameter of the user.

For a first example, when the analyzing module 102 determines that the value of pupil diameter of the user is greater than or equal to 2 mm and less than or equal to 3 mm (i.e., [2 to 3 mm]), the processing module 103 can determine that the user is in an environment with strong or bright light. The processing module 103 can increase a current brightness value of the backlight of the display screen 11. For a second example, when the analyzing module 102 determines that the value of pupil diameter of the user is greater than 3 mm and less than or equal to 5 mm (i.e., (3 to 5 mm]), the processing module 103 can determine that the user is in a comfortable environment. The processing module 103 can keep the current brightness value of the backlight of the display screen 11 or slightly adjust the current brightness value of the backlight of the display screen 11. For a third example, when the analyzing module 102 determines that the value of pupil diameter of the user is greater than 5 mm and less than or equal to 8 mm (i.e., (5 to 8 mm]), the processing module 103 can determine that the user is in an environment with low light. The processing module 103 can decrease the current brightness value of the backlight of the display screen 11.

Figure 5:
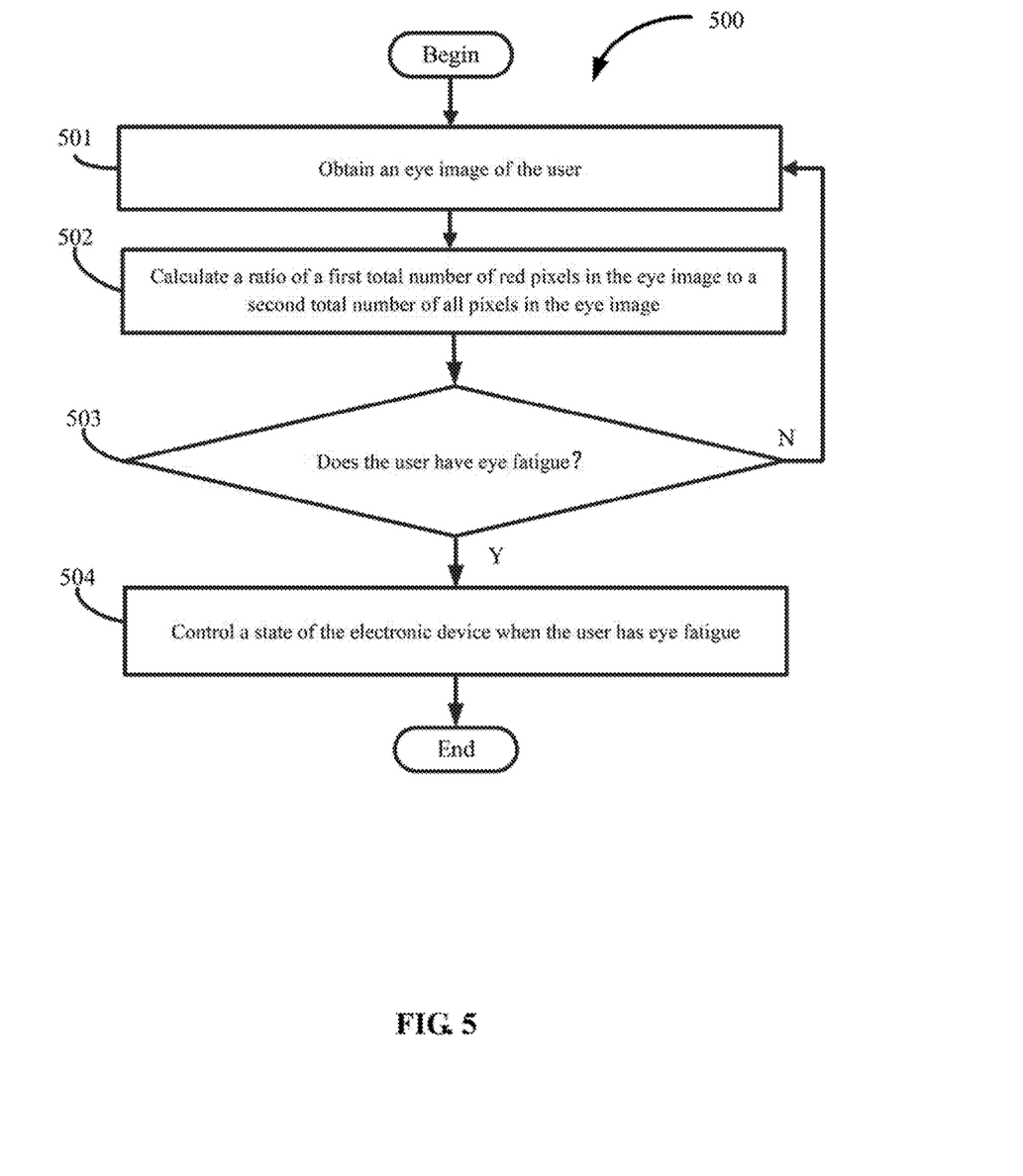
FIG. 5 illustrates a flow chart of one exemplary embodiment of a second method of adjusting a display screen of the electronic device of FIG. 1.

After the blocks 401-403 are executed, to determine whether the user is adapted to the display screen 11 that has been adjusted, the method of adjusting the display screen 11 can further include blocks 404-406. Blocks 404-406 illustrate a first exemplary embodiment of further adjusting the display screen 11 according to an eye action. A second exemplary embodiment of further adjusting the display screen 11 according to a determining result of whether the user has eye fatigue is illustrated in FIG. 5.

At block 404, the obtaining module 101 can obtain an eye image of the user.

It should be noted that the method of obtaining the eye image of the user is similar to the method of obtaining the pupil image. When the eye area is recognized from the face area, the obtaining module 101 can clip or extract the eye area from the face area, thus the eye image is obtained.

At block 405, the analyzing module 102 can determine an eye action by analyzing the eye image. In at least one exemplary embodiment, the eye action can include, but is not limited to, frowning, narrowing eye, and closing eye.

In at least one exemplary embodiment, the analyzing module 102 can pre-store a number of image templates. The number of image templates includes frown images, eye narrowing images, and eye closing images. The frown image can be defined as an image of eye area in which the user frowns. The eye narrowing image can be defined as an image of eye area in which the user narrows his/her eyes. The eye closing image can be defined as an image of eye area in which the user closes at least one eye. In at least one exemplary embodiment, the analyzing module 102 can determine that the user frowns in the eye image when the eye image matches one of the frown images templates. Similarly, the analyzing module 102 can determine that the user narrows eyes in the eye image when the eye image matches one of the eye narrowing images templates. The analyzing module 102 can determine that the user closes eyes in the eye image when the eye image matches one of the eye closing images templates.

At block 406, the processing module 103 can adjust the display screen 11 by adjusting the brightness value of the backlight of the display screen 11 and/or the proportions between RGB of the display screen 11 according to the determined eye action. For example, when the user is determined to be closing his/her eye, the processing module 103 can inactivate the display screen 11 to save power for the electronic device 1.

FIG. 5 illustrates the second exemplary embodiment of further adjusting the display screen 11 according to the determining result of whether the user has eye fatigue. The example method 500 is provided by way of example, as there are a variety of ways to carry out the method. The method 500 described below can be carried out using the configurations illustrated in FIG. 1, for example, and various elements of these figures are referenced in explaining exemplary method 500. Each block shown in FIG. 5 represents one or more processes, methods, or subroutines, carried out in the exemplary method 500. Additionally, the illustrated order of blocks is by example only and the order of the blocks can be changed according to the present disclosure. The exemplary method 500 can begin at block 501. Depending on the embodiment, additional steps can be added, others removed, and the ordering of the steps can be changed.

At block 501, the obtaining module 101 can obtain an eye image of the user.

At block 502, the analyzing module 102 can calculate a ratio between a first total number of red pixels of the eye image and a second total number of all pixels of the eye image.

In at least one exemplary embodiment, the analyzing module 102 can first find the red pixels from the eye image according to the RGB value of each of the pixels of the eye image. The analyzing module 102 can calculate the first total number of the red pixels and the second total number of all pixels of the eye image. Thus, the analyzing module 102 can calculate the ratio using the first total number and the second total number. The analyzing module 102 can divide the first total number by the second total number to obtain the ratio.

At block 503, the analyzing module 102 can determine whether the user has eye fatigue according to the ratio. In at least one exemplary embodiment, the analyzing module 102 can determine that the user has eye fatigue when the ratio is greater than a preset ratio (for example, 70%). The analyzing module 102 can determine that the user does not have eye fatigue when the ratio is less than or equal to the preset ratio. When the user has eye fatigue, the process goes to block 504. When the user does not have eye fatigue, the process goes to block 501.

It should be noted that when the user has eye fatigue due to lack of sleep, the eye area is bloodshot. Thus the ratio can be used to determine whether the user has eye fatigue.

At block 504, when the user has eye fatigue, the processing module 103 can transmit a prompt to prompt the user to stop using the electronic device 1. For example, the processing module 103 can display a preset message on the display screen 11 or can play a predetermined audio message such as "you are suffering eye fatigue, please have a rest". The processing module 103 can control the electronic device 1 to enter a sleep state when the user has eye fatigue. In at least one exemplary embodiment, the processing module 103 can further wake up the electronic device 1 from the sleep state when the electronic device 1 is kept in the sleep state for a predetermined time length (for example, 10 minutes).

It should be emphasized that the above-described embodiments of the present disclosure, including any particular embodiments, are merely possible examples of implementations, set forth for a clear understanding of the principles of the disclosure. Many variations and modifications can be made to the above-described embodiment(s) of the disclosure without departing substantially from the spirit and principles of the disclosure. All such modifications and variations are intended to be included herein within the scope of this disclosure and protected by the following claims.

What is claimed is:

1. A method for adjusting a display screen of an electronic device, the method comprising:
    obtaining a pupil image of a user of the electronic device;
    determining an eye condition of the user by analyzing the pupil image;
    adjusting proportions between a red channel, a green channel, and a blue channel (RGB) of the display screen according to the eye condition;
    obtaining an eye image of the user;
    determining eyes of the user are closed by analyzing the eye image;
    inactivating the display screen when the eyes of the user are closed;
    determining the user has eye disease when a grayscale of a first predetermined portion of the pupil image is within a first preset range;
    determining the user not has eye disease when the grayscale of the first predetermined portion of the pupil image is within a second preset range, wherein the second preset range is different from the first preset range;
    determining the user has eye disease when a red chroma of a second predetermined portion of the pupil image is within a third preset range;
    determining the user is wearing contact lens when a blue chroma of the pupil image is within a fourth preset range;
    recording a start time when the user is determined to be wearing contact lens;
    obtaining a first pupil image of the user when the start time is recorded;
    obtaining a second pupil image of the user when a time length calculated beginning from the start time equals a preset time length;
    determining the user has been wearing contact lens for the preset time length when the user is determined to be wearing contact lens both in the first pupil image and the second pupil image; and
    transmitting a prompt when the user is determined to have been wearing contact lens for the preset time length.

2. The method according to claim 1, further comprising:
    adjusting the proportions between RGB by decreasing the blue channel of the display screen when the user is determined to have eye disease; and
    not adjusting the display screen when the user is determined not to have eye disease.

3. The method according to claim 1, further comprising:
    determining a pupil diameter of the user in the pupil image; and
    adjusting a brightness value of a backlight of the display screen according to the pupil diameter of the user.

4. The method according to claim 1,
    wherein when the eye image matches one pre-stored image template of eyes closed, the eyes of the user are determined to be closed.

5. The method according to claim 1, further comprising:
    obtaining an eye image of the user;
    calculating a ratio of a first total number of red pixels in the eye image to a second total number of all pixels in the eye image;
    determining whether the user has eye fatigue according to the ratio; and
    controlling a state of the electronic device when the user has eye fatigue.

6. The method according to claim 5, further comprising:
    controlling the electronic device to enter a sleep state when the user has eye fatigue; and
    waking up the electronic device from the sleep state when the electronic device is kept the sleep state for a predetermined time length.

7. An electronic device comprising:
    a display screen;
    a storage device;
    at least one processor; and
    the storage device storing one or more programs, which when executed by the at least one processor, cause the at least one processor to:
    obtain a pupil image of a user of the electronic device;
    determine an eye condition of the user by analyzing the pupil image;
    adjust proportions between a red channel, a green channel, and a blue channel (RGB) of the display screen according to the eye condition;
    obtain an eye image of the user;
    determine eyes of the user are closed by analyzing the eye image;
    inactivate the display screen when the eyes of the user are closed;
    determining the user has eye disease when a grayscale of a first predetermined portion of the pupil image is within a first preset range;
    determining the user not has eye disease when the grayscale of the first predetermined portion of the pupil image is within a second preset range, wherein the second preset range is different from the first preset range;
    determining the user has eye disease when a red chroma of a second predetermined portion of the pupil image is within a third preset range;
    determining the user is wearing contact lens when a blue chroma of the pupil image is within a fourth preset range;
    record a start time when the user is determined to be wearing contact lens;
    obtain a first pupil image of the user when the start time is recorded;
    obtaining a second pupil image of the user when a time length calculated beginning from the start time equals a preset time length;
    determine the user has been wearing contact lens for the preset time length when the user is determined to be wearing contact lens both in the first pupil image and the second pupil image; and
    transmit a prompt when the user is determined to have been wearing contact lens for the preset time length.

8. The electronic device according to claim 7, wherein the at least one processor is further caused to:
   adjust the proportions between RGB by decreasing the blue channel of the display screen when the user is determined to have eye disease; and
   not adjust the display screen when the user is determined not to have eye disease.

9. The electronic device according to claim 7, wherein the at least one processor is further caused to:
   determine a pupil diameter of the user in the pupil image; and
   adjust a brightness value of a backlight of the display screen according to the pupil diameter of the user.

10. The electronic device according to claim 7,
   wherein when the eye image matches one pre-stored image template of eyes closed, the eyes of the user are determined to be closed.

11. The electronic device according to claim 7, wherein the at least one processor is further caused to:
   obtain an eye image of the user;
   calculate a ratio of a first total number of red pixels in the eye image to a second total number of all pixels in the eye image;
   determine whether the user has eye fatigue according to the ratio; and
   control a state of the electronic device when the user has eye fatigue.

12. The electronic device according to claim 11, wherein the at least one processor is further caused to:
   control the electronic device to enter a sleep state when the user has eye fatigue; and
   wake up the electronic device from the sleep state when the electronic device is kept in the sleep state for a predetermined time length.

* * * * *